United States Patent [19]

Desai

[11] Patent Number: 5,202,440
[45] Date of Patent: Apr. 13, 1993

[54] CERTAIN 9-AMINO-2-(OR 4)-OXA 1,2,3,4-TETRAHYDRO- OR 1,2,3,4,5,6,7,8-OCTAHYDRO-ACRIDINES

[75] Inventor: Manoj C. Desai, Mystic, Conn.

[73] Assignee: Pfizer Inc., New York, N.Y.

[21] Appl. No.: 474,717

[22] PCT Filed: Mar. 30, 1988

[86] PCT No.: PCT/US88/01070

§ 371 Date: Apr. 27, 1990

§ 102(e) Date: Apr. 27, 1990

[87] PCT Pub. No.: WO89/02740

PCT Pub. Date: Apr. 6, 1989

[30] Foreign Application Priority Data

Oct. 5, 1987 [WO] PCT Int'l Appl. ............... PCT/US87/02546

[51] Int. Cl.[5] ............... C07D 491/052; A61K 31/44
[52] U.S. Cl. ............... 546/89; 546/80; 546/81; 546/82; 546/83; 546/84; 546/93; 546/104; 514/291
[58] Field of Search ............... 546/89; 514/291

[56] References Cited

U.S. PATENT DOCUMENTS

| | | | |
|---|---|---|---|
| 3,232,945 | 2/1966 | Sigal, Jr. et al. | 546/93 |
| 3,318,896 | 5/1967 | Pribyl et al. | 546/93 |
| 3,541,066 | 11/1970 | Wolf | 546/63 |
| 3,580,915 | 5/1971 | Wolf et al. | 546/63 |
| 4,180,580 | 12/1979 | Demerson et al. | 514/291 |
| 4,550,113 | 10/1985 | Lavretskaya et al. | 514/290 |
| 4,578,394 | 3/1986 | Allen et al. | 514/332 |
| 4,631,286 | 12/1986 | Shutske et al. | 514/297 |
| 4,652,567 | 3/1987 | Martin et al. | 514/254 |
| 4,680,297 | 7/1987 | Blythin et al. | 514/293 |
| 4,680,298 | 7/1987 | Blythin et al. | 514/293 |
| 4,695,573 | 9/1987 | Shutske et al. | 514/290 |
| 4,753,950 | 6/1988 | Shutske et al. | 514/291 |

FOREIGN PATENT DOCUMENTS

| | | | |
|---|---|---|---|
| 0179383 | 4/1986 | European Pat. Off. | 546/105 |
| 0268871 | 6/1988 | European Pat. Off. | 546/105 |
| 0273176 | 7/1988 | European Pat. Off. | 546/82 |
| 0278499 | 8/1988 | European Pat. Off. | 540/493 |
| 0282959 | 9/1988 | European Pat. Off. | 546/105 |
| 0287977 | 10/1988 | European Pat. Off. | 546/89 |

OTHER PUBLICATIONS

Indian Journal of Chemistry, vol. 26B Oct. 1987 pp. 910–913.
Chem. Abst. vol. 69 No. 25 Abst. No. 106408d, 1968.
Chem. Abstracts, vol. 92 No. 1, Abst. No. 6385a; Arne Osbirk et al., 1980.
Chem. Abstracts, vol. 108, Abst. No. 124385x, 1988.

Primary Examiner—Alan L. Rotman
Attorney, Agent, or Firm—Peter C. Richardson; Paul H. Ginsburg; Valerie M. Fedowich

[57] ABSTRACT

Compounds selected from the group consisting of 9-amino-4-oxa-1,2,3,4-tetrahydro-acridine, 9-amino-2-oxa-1,2,3,4-tetrahydro-acridine, 9-amino-8-fluoro-4-oxa-1,2,3,4-tetrahydro-acridine, 9-amino-4-oxa-1,2,3,4,5,6,7,8-octahydro-acridine or a pharmaceutical acceptable salt thereof are useful treating Alzheimer's disease.

1 Claim, No Drawings

CERTAIN 9-AMINO-2-(OR 4)-OXA 1,2,3,4-TETRAHYDRO- OR 1,2,3,4,5,6,7,8-OCTAHYDRO-ACRIDINES

BACKGROUND OF THE INVENTION

The present invention relates to 4-aminopyridine derivatives. The compounds of the present invention inhibit brain acetylcholinesterase and are useful in the treatment of Alzheimer's disease.

Tetrahydroaminoacridine, which has anticholinesterase activity, has been reported to produce improved performance in psychological tests in patients afflicted with Alzheimer's disease (W. K. Summers et al., *The New England Journal of Medicine*, 315, 1241–1245 (1986)). The anticholinesterase physostigmine has also been reportedly used in the experimental treatment of Alzheimer's disease (S. D. Brinkman et al., *Neurobiol. Aging*, 4, 139–145 (1983)).

The compounds described in the following four documents are alleged to have anticholinesterase activity:

U.S. Pat. No. 4,652,567 refers to benzo(C)-1,5-naphthyridines for treating Alzheimer's disease.

U.S. Pat. No. 4,631,286 refers to 9-amino-1,2,3,4-tetrahydroacridine-1-ol and related compounds for treating Alzheimer's disease.

U.S. Pat. No. 4,550,113 refers to 9-amino-2,3,5,6,7,8-hexahydro-1H-cyclopenta(b)quinoline monohydrate hydrochloride for treating neuritis, injuries of the peripheral nervous system, hereditary neuromuscular diseases, and disseminated sclerosis.

U.S. Pat. No. 4,578,394 refers to dihydropyridines for treating Alzheimer's disease.

U.S. Pat. No. 4,540,564 refers to dihydropyridines for delivering drugs to the brain.

G. K. Patnaik et al., *J. Med. Chem.*, 9, 483–488 (1966), refer to 4-substituted 2,3-polymethylenequinolines having analgetic, local anesthetic, analeptic, and respiratory stimulant activities.

British Patent Specifications 1,186,061, 1,186,062, and 1,186,063 refer to benzonaphthyridine derivatives.

SUMMARY OF THE INVENTION

The present invention relates to compounds of the formula

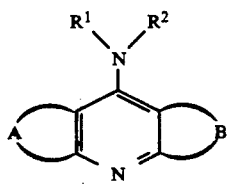

wherein A is selected from the group consisting of

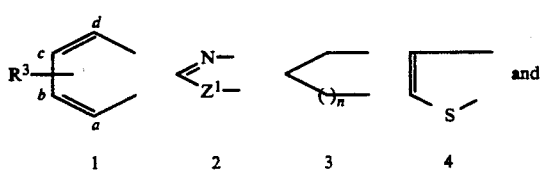

-continued

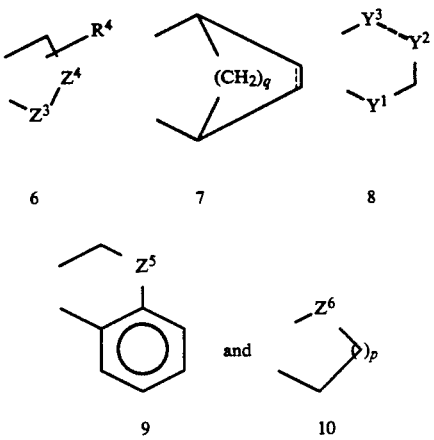

wherein one of the CH moieties at positions a, b, c and d of formula 1 may be replaced by a nitrogen atom or each of the CH moieties at positions a and d, a and c or b and d may be replaced by a nitrogen atom; B is selected from the group consisting of wherein each broken line represents an optional double bond; $R^1$ is hydrogen or $C_1$–$C_6$ alkyl; $R^3$ is independently selected from the group consisting of hydrogen, $C_1$–$C_6$ alkyl, $C_1$–$C_6$ alkoxy, $C_1$–$C_6$ alkanoyl, di($C_1$–$C_6$ alkylamino)-$C_1$–$C_6$ alkyl, $C_1$–$C_6$ alkoxy-$C_1$–$C_6$ alkyl, halogen (e.g., fluoro, chloro, bromo or iodo), hydroxy, nitro, phenyl, substituted phenyl, phenyl-$C_1$–$C_6$ alkyl, substituted phenyl-$C_1$–$C_6$ alkyl, diphenyl-$C_1$–$C_6$ alkyl wherein one or both of the phenyl groups may be replaced with a substituted phenyl group, furyl-$C_1$–$C_6$ alkyl, thienyl-$C_1$–$C_6$ alkyl, phenyloxy, substituted phenyloxy, $NHCOR^5$ and $NR^6R^7$, wherein the phenyl moieties on the substituted phenyl and substituted phenylalkyl groups are substituted with one or more substituents (preferably, one or two substituents) selected from the group consisting of halogen (e.g., fluoro, chloro, bromo or iodo), $C_1$–$C_6$ alkyl, trifluoromethyl, $C_1$–$C_6$ alkoxy-$C_1$–$C_6$ alkyl, hydroxy and nitro, and wherein $R^5$, $R^6$ and $R^7$ are independently selected from $C_1$–$C_6$ alkyl and $C_1$–$C_6$ alkanoyl; $R^2$ is independently selected from the group consisting of 1,4-dihydropyridyl-$C_1$–$C_6$ alkanoyl, $C_1$–$C_6$ alkyl-1,4-dihydropyridyl-$C_1$–$C_6$-alkanoyl, and the possible definitions set forth above for $R^3$, except that $R^2$ cannot be hydroxy, halogen, $C_1$–$C_6$ alkoxy, phenyloxy or substituted phenyloxy; $R^4$ is independently selected from the possible definitions set forth above for $R^3$, except that $R^4$ cannot be halogen, nitro, $NHCOR^5$ or $NR^6R^7$; n is 1, 2 or 3; $Z^1$ is NH, O, S or $NR^8$ wherein $R^8$ is $C_1$–$C_6$ alkyl or $C_1$–$C_6$ alkanoyl; $Z^2$ is O or S; $Z^3$ are independently selected from $(CH_2)_p$, O, S, S=O and $SO_2$, with the proviso that at least one of $Z^3$ and $Z^4$ is $(CH_2)_p$; $Z^5$ is $CH_2$, O, S, S=O or $SO_2$; $Z^6$ is O, S, S=O or $SO_2$; p is 1, 2 or 3; q is 1 or 2; $Y^1$ is $CH_2$, CHOH, O, C=O, S, S=O or $SO_2$; $Y^2$ is $CH_2$, CH, O, S, S=O or $SO_2$; and $Y^3$ is CHOH, $CH_2$, CH or C=O, with the proviso that the group of the formula 8 may have a double bond only when both $Y^2$ and $Y^3$ are CH, with the proviso that when A is a group of the formula 1 wherein $R^3$ is hydrogen and there is no nitrogen at position a, b, c or d or A is a group of the formula 3 or 4, only one of $Y^1$ and $Y^2$ can be $CH_2$, and with the proviso that when A is a group of the formula 1 wherein $R^3$ is hydrogen and there is no nitrogen at position a, b, c, or d, only one of $Z^3$ and $Z^4$ can be $(CH_2)_p$; and pharmaceutically acceptable salts thereof.

The present invention also relates to a pharmaceutical composition for the treatment of Alzheimer's disease comprising a compound of the formula I and to the use of compounds of the formula I in treating Alzheimer's disease. The present invention also relates to methods of preparing compounds of the formula I.

One embodiment of the present invention relates to compounds of the formula I wherein $R^1, R^2$, A and B are as defined for formula I, with the proviso that when A is a group of the formula 1 wherein there is no nitrogen at position a, b, c or d or A is a group of the formula 3 or 4, only one of $Y^1$ and $Y^2$ can be $CH_2$; and pharmaceutically acceptable salts thereof. One aspect of the foregoing embodiment relates to compounds wherein $Y^3$ is $CH_2$, and at least one of $Z^3$ and $Z^4$ is $CH_2$; with the proviso that when A is a group of the formula 1 wherein $R^3$ is hydrogen and there is no nitrogen at position a, b, c or d, only one of $Z^3$ and $Z^4$ can be $(CH_2)_p$.

A preferred embodiment of the present invention relates to compounds of the formula I wherein A, B, $Z^1$, $Z^2$, $Z^3$, $Z^4$, $Z^5$, $Z^6$ and $Y^3$ are as defined with respect to formula I; $R^1$, $R^2$ and $R^4$ are hydrogen; and $R^3$ is hydrogen or halogen; with the proviso that when A is a group of the formula 1 wherein there is no nitrogen at position a,b,c or d, or A is a group of the formula 3 or 4, only one of $Y^1$ and $Y^2$ can be $CH_2$; and pharmaceutically acceptable salts thereof. When $R^3$ is halogen, the halogen is preferably fluorine.

Another preferred embodiment of the present invention relates to compounds of the formula I wherein
A is a group of the formula 1, wherein one of the CH moieties at positions a and b of formula 1 may be replaced by a nitrogen atom, or A is a group of the formula 3;
B, $R^1$, $R^2$, $R^3$, $R^4$, $Z^3$, $Z^4$, $Z^5$, $Y^3$ and q are as defined with respect to formula I;
n is 1 or 2; $Z^6$ is S; and p is 1 or 2; with the proviso that
(a) when A is a group of the formula 1 wherein there is no nitrogen at either position a or position b, $Z^3$ is O, S or $CH_2$; $R^4$ is hydrogen or $C_1$-$C_6$ alkyl; $Z^4$ is $(CH_2)_p$, wherein p is 1 or 2, or S; $Y^1$ is $CH_2$, C=O, O, or S, and $Y^2$ is $CH_2$, O or S, with the proviso that only one of $Y^1$ and $Y^2$ can be $CH_2$;
(b) when A is a group of the formula 1 wherein there is a nitrogen at either position a or position b, $Y^1$ is O, S or $CH_2$ and $Y^2$ is $CH_2$; and
(c) when A is a group of the formula 3, $Y^1$ is O or S; and $Y^2$ is $CH_2$;
and the pharmaceutically acceptable salts thereof. In a more preferred embodiment, $R^1$, $R^2$ and $R^4$ are hydrogen and $R^3$ is hydrogen or halogen. When $R^3$ is halogen, the halogen is preferably fluorine.

Another preferred embodiment of the present invention relates to compounds of the formula I, wherein B is a group of the formula 7 or 8 and A, $R^1$, $R^2$, $R^3$, $Z^1$, $Z^2$, q, $Y^1$, $Y^2$ and $Y^3$ are as defined with respect to formula I, with the proviso that when A is a group of the formula 1 wherein there is no nitrogen at position a, b, c, or d, or A is a group of the formula 3 or 4, only one of $Y^1$ and $Y^2$ can be $CH_2$; and pharmaceutically acceptable salts thereof. In a more preferred embodiment, $R^1$ and $R^2$ are hydrogen and $R^3$ is hydrogen or halogen. When $R^3$ is halogen, the halogen is preferably fluorine.

A particularly preferred embodiment of the present invention relates to compounds of the formula I, wherein A is a group of the formula 1, wherein one of the CH moieties at positions a and b of formula 1 may be replaced by a nitrogen atom, or A is a group of the formula 3; B is a group of the formula 7 or 8; $R^1$, $R^2$, $R^3$, q, $Y^1$, $Y^2$ and $Y^3$ are as defined for formula I; and n is 1 or 2; with the proviso that
(a) when A is a group of the formula 1 wherein there is no nitrogen at either position a or position b, $Y^1$ is $CH_2$, C=O, O or S, and $Y^2$ is $CH_2$, O or S, with the proviso that only one of $Y^1$ and $Y^2$ can be $CH_2$;
(b) when A is a group of the formula 1 wherein there is a nitrogen at either position a or position b, $Y^1$ is O, S or $CH_2$ and $Y^2$ is $CH_2$; and
(c) when A is a group of the formula 3, $Y^1$ is O or S; and $Y^2$ is $CH_2$;
and the pharmaceutically acceptable salts thereof. In a more preferred embodiment, $R^1$, $R^2$ and $R^4$ are hydrogen and $R^3$ is hydrogen or halogen. When $R^3$ is halogen, the halogen is preferably fluorine.

Another preferred embodiment of the present invention relates to compounds of the formula I, wherein A is a group of the formula 1, wherein $R^3$ is as defined for formula I, with the proviso that $R^3$ may only be at position d of formula 1, and $R^1, R^2$ and B are as defined for formula I, and the pharmaceutically acceptable salts thereof. In a more preferred embodiment, $R^3$ is halogen, more preferably, fluorine.

Another preferred embodiment of the present invention relates to compounds of the formula I, wherein A is a group of the formula 1, wherein $R^3$ is selected from the group consisting of $C_1$-$C_6$ alkyl, $C_1$-$C_6$ alkoxy, halogen, hydroxy, nitro, $NHCOR^5$, $NR^6R^7$ or trifluoromethyl; B is a group of the formula

wherein r is 2,3 or 4; and $R^1, R^2, R^5, R^6$ and $R^7$ are as defined for formula I; and the pharmaceutically acceptable salts thereof. Of the foregoing compounds the more preferred compounds are those wherein $R^3$ is at the d position of formula 1 or wherein $R^3$ is halogen. Particularly preferred compounds are those wherein $R^3$ is halogen at the d position. When $R^3$ is halogen, the halogen is preferably fluorine.

Specific preferred compounds of the present invention are the following:
9-amino-4-oxa-1,2,3,4-tetrahydroacridine;
9-amino-1,2,3,4-tetrahydro-1,4-methanoacridine;
9-amino-8-fluoro-1,2,3,4-tetrahydro-1,4-methanoacridine;
9-amino-2-oxa-1,2,3,4,-tetrahydroacridine;
9-amino-2-thia-1,2,3,4-tetrahydroacridine;
9-amino-8-fluoro-4-oxa-1,2,3,4-tetrahydroacridine;
9-amino-4-oxa-1,2,3,4,5,6,7,8-octahydroacridine;
2,3-dihydrothieno[3,2-b]quinoline-9-amine;
9-amino-5-aza-1,2,3,4-tetrahydroacridine;
2,3-dihydro-8-fluoro-thieno[3,2-b]quinolin-9-amine;
9-amino-1,2-dihydroacridine-4(3H)-one;

1,3-dihydro-8-fluoro-thieno[3,4-b]quinolin-9-amine;
9-amino-4-thia-1,2,3,4-tetrahydroacridine;
8-fluoro-9-amino-1,2,3,4-tetrahydroacridine; and
9-amino-8-fluoro-2-thia-1,2,3,4-tetrahydroacridine.

Other compounds of the present invention are the following:
9-amino-4,5-thiaza-1,2,3,4-tetrahydroacridine;
9-amino-4-thia-1,2,3,4,5,6,7,8-octahydroacridine;
9-amino-2-thia-1,2,3,4,5,6,7,8-octahydroacridine;
9-amino-2-oxa-1,2,3,4,5,6,7,8-octahydroacridine;
9-amino-5,7-diaza-1,2,3,4-tetrahydroacridine;
9-amino-3-methyl-7-phenyl-4-oxa-1,2,3,4-tetrahydroacridine;
9-amino-6-trifluoromethyl-1,4-methano-1,2,3,4-tetrahydroacridine;
9-amino-5,8-diaza-1,4-methano-1,2,3,4-tetrahydroacridine;
9-amino-1-thia-1,2,3,4-tetrahydroacridine;
9-amino-3-thia-1,2,3,4-tetrahydroacridine;
4-amino-5,6,7,8-tetrahydro-1H-imidazo[4,5-b]quinoline;
4-amino-5,6,7,8-tetrahydro-oxazolo[4,5-b]quinoline;
4-amino-5,6,7,8-tetrahydro-thiazolo[4,5-b]quinoline;
9-amino-1,2,3,4-tetrahydroacridine-4-ol;
9-amino-6-trifluoromethyl-4-oxa-1,2,3,4-tetrahydroacridine;
9-amino-6-trifluoromethyl-1-hydroxy-4-oxa-1,2,3,4-tetrahydroacridine; and
9-amino-1-hydroxy-4-oxa-1,2,3,4-tetrahydroacridine.

Preferred compositions of the present invention contain the foregoing preferred compounds. More preferred compositions of the present invention contain the foregoing more preferred compounds and specific preferred compounds.

DETAILED DESCRIPTION OF THE INVENTION

Compounds of the present invention may be prepared as described below.

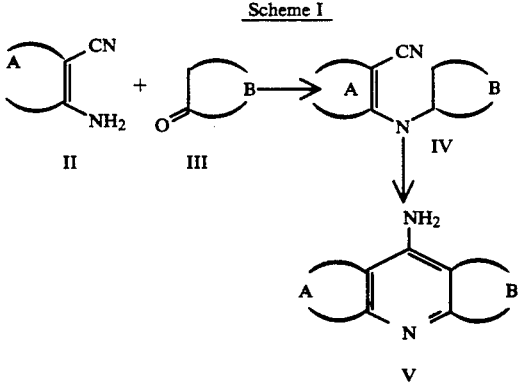

Scheme I

As shown in Scheme I, an aminonitrile of the formula II, wherein A is as defined above, is reacted with a ketone of the formula III wherein B is as defined above to prepare a ketimine of the formula IV. The reaction is conducted in an inert solvent, preferably an aromatic solvent (e.g., benzene or toluene), in the presence of an acid, preferably a strong acid (e.g. p-toluenesulfonic acid). The temperature should be at least about 100° C., but is otherwise not critical. Generally, the reaction is conducted at the reflux temperature of the reaction mixture, e.g., by refluxing the reaction mixture in a Dean Stark apparatus, preferably for about 6 to about 16 hours, and removing the water periodically. The reaction pressure is not critical. Generally, the reaction will be conducted at a pressure of about 0.5 to about 2 atmospheres, preferably at ambient pressure (generally, about 1 atmosphere).

The crude ketimine IV obtained after the removal of solvent is then reacted with a base (e.g., lithium diisopropylamide) in an inert solvent, preferably an anhydrous ether (e.g., tetrahydrofuran), at a temperature of about 0° C. to about 25° C. The reaction pressure is not critical. Generally, the reaction will be conducted at a pressure of about 0.5 to about 2 atmospheres, preferably at ambient pressure (generally, about 1 atmosphere).

The first method works especially well when an all carbon ketone is employed in the reaction. Azeotropic removal (80° C., PTSA, 15 hours) of water from a benzene solution of norcamphor (or an all carbon ketone) and anthranilonitrile afforded the corresponding ketimine which on treatment with lithium diisopropylamide (0° C., 4 hours) in tetrahydrofuran afforded the compound of Example 1 in 25% yield. The use of this procedure is also exemplified by the preparation of the compounds of Examples 2, 3, 4, 30 and 36.

The limitation in the general applicability of the first method is the difficulty of formation of ketimines from carbonyl compounds containing a nitrogen or oxygen atom. Titanium (IV) chloride, because of its high affinity for oxygen, has been used in the preparation of ketimines. (See H. Weingarten et al., J. Org. Chem., 32, 3246(1967)). This observation was adapted for the synthesis of 9-amino-1,2,3,4-tetrahydroacridine derivatives in a single step by the condensation of appropriate o-aminonitriles with diverse carbonyl components.

Thus, in a second method for preparing compounds of the present invention, a compound of the formula II wherein A is defined as above is reacted with a carbonyl-containing compound of the formula III wherein B is as defined above. The carbonyl-containing compound may be a ketone, a lactone, or the like. The reaction is conducted in an inert solvent in the presence of a Lewis acid (e.g., titanium (IV) chloride) and, if necessary, in the presence of a base, preferably an amine base (e.g. triethylamine). Suitable solvents include aromatic solvents (e.g., benzene or toluene) and chlorinated solvents (e.g., methylene chloride or 1,2-dichloroethane). The reaction temperature should be at least about 0° C. and is preferably about 25° to about 120° C. The reaction pressure is not critical. Generally, the reaction will be conducted at a pressure of about 0.5 to about 2 atmospheres, preferably at ambient pressure (generally, about 1 atmosphere).

Thus, for example, condensation of deltavalerolactone with anthranilonitrile in methylene chloride by titanium (IV) chloride at 25° C. in the presence of triethylamine (2 equivalents) afforded the compound of Example 7 (28%). This method was adopted for the synthesis of the compounds of Examples 7-19, 26-29, 31-33, 35 and 37-46. The compounds of Examples 5 and 6 were prepared by condensing anthranilonitrile with the appropriate ketones in the presence of anhydrous zinc chloride at elevated temperature (<140° C.).

Monoalkylation of the amine group in compounds of the present invention may be achieved by heating them with appropriate alkyl halides in the presence of sodium hydride in dimethylformamide. This is exemplified by the synthesis of the compounds of Examples 20-25 and 34.

The compounds of Formula I are capable of forming acid addition salts with pharmaceutically acceptable acids. The acid addition salts may be prepared by reacting the base form of the appropriate compound of formula I with one or more equivalents, preferably with an excess, of the appropriate acid in an organic solvent, for example, diethyl ether or an ethanol diethyl ether mixture. Suitable acids to form these salts include the common mineral acids, e.g. hydrohalic, sulfuric or phosphoric acid; the organic acids, e.g. ascorbic, citric, lactic, aspartic or tartaric acid or their aqueous solutions whose pH has been adjusted to 5.5 or less; and acids which are sparingly soluble in body fluids and which impart slow-release properties to their respective salts, e.g. pamoic or tannic acid or carboxymethyl cellulose. The preferred salt is the hydrochloride salt.

The compounds of formula I and the pharmaceutically acceptable salts thereof are useful in the treatment of various memory dysfunctions associated with decreased cholinergic function such as Alzheimer's Disease. Additionally, the compounds lead to stimulation of neuromuscular transmission, enhancement of excitation in excitable tissues (nerve, and smooth and striated muscle) as well as restoration of conductance in nerves and neuromuscular synapses in the case of injury thereof. The compounds of this invention also exhibit antidepressant activities which is particularly helpful for patients suffering from Alzheimer's Disease. The compounds of this invention are, in general, less toxic and have a broader therapeutic window than known compounds such as tacrine and physotigmine, making them therapeutically preferred.

In treating Alzheimer's disease, the dosage of the compounds of the present invention will vary with the form of administration and the particular compound chosen. Furthermore, it will vary with the particular subject as well as the age, weight and condition of the subject under treatment as well as with the nature and extent of the symptoms. Generally, however, a dose in the range of about 1 to about 300 mg/day, taken in single or divided doses, will be administered. The preferred dose is in the range of from about 1 to about 150 mg/day in single or divided doses.

Generally, treatment is initiated with small dosages substantially less than the optimum dose of the compound. Thereafter, the dosage is increased by small increments until the optimum effect under the circumstances is reached.

The compounds of the present invention are used alone or in combination with pharmacologically acceptable carriers, the proportion of which is determined by the solubility and chemical nature of the compound, chosen route of administration and standard medical practice. For example, they are administered orally in the form of capsules, tablets, suspensions or solutions or they may be injected parenterally. Capsules and tablets are the preferred mode of administration. For parenteral administration, they can be used in the form of a sterile solution containing other solutes, for example, enough saline or glucose to make the solution isotonic.

Capsule and tablet compositions may contain the active ingredient in admixture with one or more pharmaceutical excipients suitable for the manufacture of capsules and tablets. Suitable pharmaceutical excipients are, for example, starch, milk sugar, and certain types of clay. The tablets can be uncoated or they can be coated by known techniques so as to delay disintegration and absorption in the gastrointestinal tract and thereby provide a sustained action over a longer period.

Aqueous suspensions of the compounds of formula I contain the active ingredient in admixture with one or more pharmaceutical excipients suitable for the manufacture of aqueous suspensions. Suitable excipients are, for example, methylcellulose, sodium alginate, gum acacia, lecithin and so forth. Aqueous suspensions can also contain one or more preservatives, one or more coloring agents, one or more flavoring agents and one or more sweetening agents.

Non-aqueous suspensions can be formulated by suspending the active ingredient in a vegetable oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

The following examples illustrate the preparation and properties of the compounds of the present invention. All melting points are uncorrected. Thin layer chromatography (TLC) was conducted on silica gel.

EXAMPLE 1

9-Amino-1,2,3,4-tetrahydro-1,4-methanoacridine

A solution of anthranilonitrile (3.6 g, 30.0 mmole), norcamphor (3.3 g, 30.0 mmole) and para-toluenesulfonic acid (50 mg) in benzene (50 ml) was heated to reflux using a Dean Stark apparatus. After heating for 18 hours, the reaction mixture was then cooled (25° C.) and the separated water (about 1.5 ml) was withdrawn. The excess benzene was then removed under vacuum (1 mm Hg, 15 minutes). The oily residue thus obtained was dissolved in tetrahydrofuran (THF, 10 ml) and was cooled to 0° C. and a solution of lithium diisopropylamide in THF (1M, 36 ml, 36 mmole) was then added. This reaction mixture was then stirred at 0° C. for 3 hours. At the end of this period, the reaction mixture was quenched with 40 ml of water and was extracted with methylene chloride (200 ml). The resulting organic phase was washed with water (2×50 ml) and dried (anhydrous $MgSO_4$). The methylene chloride was removed under vaccum to afford a residue which was loaded on a silica gel flash chromatography column. Elution with 5% methanol in methylene chloride containing 1% triethylamine afforded the title compound 1.6 g, 25%) as an oil which solidified on standing (m.p. 185°-186° C.). $^1$H-NMR ($CDCl_3$, 300 MHz, δ): 2H, m, 1.22-1.42 ppm; 1H, d, 1.64 ppm (J=7.0 Hz); 1H, d, 1.86 ppm (J=6.0 Hz); 2H, m, 1.9-2.04 ppm; 2H, bd, 3.46 ppm; 2H, bs, 4.49 ppm; 1H, t, 7.38 ppm (J=6.0 Hz); 1H, t, 7.55 ppm (J=6.0 Hz); 1H, d, 7.67 ppm (J=6.0 Hz); 1H, d, 7.92 ppm (J=6.0 Hz).

EXAMPLE 2

9-Amino-8-fluoro-1,2,3,4-tetrahydro-1,4-methanoacridine

Following the procedure of Example 1, but substituting 2-amino-6-fluorobenzonitrile for anthranilonitrile, afforded the title compound (23%, m.p. 173° C.). $^1$N-NMR ($CDCl_3$, 300 MHz, δ): 2H, m, 1.28-1.5 ppm; 1H, bd, 1.68 ppm; 1H, bd, 1.89 ppm; 2H, m, 1.98-2.18 ppm; 2H, bs, 3.5 ppm; 2H, bs, 5.18 ppm; 1H, dd, 7.0 ppm (J=12.5, 8.0 Hz); 1H, m, 7.44 ppm (J=12.5, 8.0 HZ); 1H, d, 7.75 ppm (J=8.0 Hz). HRMS: Calculated—228.1062; Found—228.1049. TLC: (90:10:1-

EXAMPLE 3

9-Amino-7-chloro-1,2,3,4-tetrahydro-1,4-methanoacridine

Following the procedure of Example 1, but substituting 2-amino-5-chlorobenzonitrile for anthranilonitrile, afforded the title compound (14%, m.p. 183°-184° C.). $^1$H-NMR (CDCl$_3$, 300 MHz, $\delta$): 2H, m, 1.3-1.56 ppm; 1H, bd, 1.65 ppm; 1H, bd, 1.92 ppm; 2H, m, 1.98-2.18 ppm; 1H, bs, 3.5 ppm; 1H, bs, 3.54 ppm; 2H, bs, 4.45 ppm; 1H, dd, 7.5 ppm (J=2, 9.0 Hz); 1h, d, 7.65 ppm (J=2 Hz); 1H, d, 7.84 ppm (J=9.0 Hz). HRMS: Calculated—244.0767; Found—244.0750. TLC: (90:10:1-methylene chloride:methanol:28% aqueous ammonia) R$_f$=0.7.

EXAMPLE 4

9-Amino-1,4-dihydro-1,4-methanoacridine

Following the procedure of Example 1, but substituting 5-norbornen-2-one for norcamphor, afforded the title compound (26%, m.p. 123° C.). $^1$H-NMR (CDCl$_3$, 300 MHz, $\delta$): 1H, d, 2.4 ppm (J=8.0 Hz), 1H, dt, 2.5 ppm (J=1.7, 8.0 Hz); 1H, bs, 3.88 ppm; 1H, bs, 4.07 ppm; 1H, bs, 4.46 ppm, 2H, s, 6.86 ppm; 1H, t, 7.44 ppm (J=8.0 Hz); 1H, t, 7.6 ppm (J=8.0 Hz); 1H, d, 7.68 ppm (J=8.0 Hz); 1H, d, 7.94 ppm (J=8.0 Hz). HRMS: Calculated—208.2622; Found—208.0974. TLC: (90:10:1-methylene chloride:methanol:28% aqueous ammonia) R$_f$=0.57.

EXAMPLE 5

9-Amino-2-oxa-1,2,3,4-tetrahydroacridine

Anthranilonitrile (25 mmole, 2.95 g), zinc chloride (3.1 g, 25 mmole) and tetrahydro-4H-pyran-4-one were dissolved in toluene (40 ml) and heated to reflux for 2.5 days. At the end of this period, the reaction mixture was cooled (25° C.), was quenched with aqueous sodium hydroxide (70 ml) and was extracted with methylene chloride (4×60 ml). The combined organic phases were washed with water (2×100 ml) and dried (anhydrous MgSO$_4$). The organic solvents were removed under vacuum to yield a yellow residue which was loaded on a silica gel flash chromatography column. Elution with 5% methanol in methylene chloride afforded the title compound as yellow crystals (155 mg, 31%, m.p. 195°-196° C.). $^1$H-NMR (CDCl$_3$, 300 MHz, $\delta$): 2H, t, 3.08 ppm (J=6.0 Hz); 2H, t, 4.06 ppm (J=6.0 Hz); 2H, bs, 4.47 ppm; 2H, s, 4.74 ppm; 1H, t, 7.34 (J=8.0 Hz); 1H, t, 7.54 (J=8.0 Hz); 1H, d, 7.64 (J=8.0 Hz); 1H, d, 7.84 (J=8.0 Hz). TLC: (TLC plate pretreated with 2% triethylamine in hexane; eluant: 5% methanol in methylene chloride) R$_f$=0.25.

EXAMPLE 6

9-Amino-2-thia-1,2,3,4-tetrahydroacridine

Anthranilonitrile (2.6 g, 21.5 mmole), tetrahydrothiopyran-4-one (5.0 g, 43 mmole) and zinc chloride (2.54 g, 21.5 mmole) were combined and heated to 120° C. for 20 minutes. The reaction mixture was cooled and the solid residue was filtered using ethyl ether (100 ml). The resulting orange solid (5.2 g) was placed in a beaker containing a saturated solution of EDTA (ethylene diamine tetracetic acid) in water (125 ml) and the pH was adjusted to 13 with the help of 12% NaOH. The aqueous phase was then extracted with methylene chloride (4×50 ml) which was washed with water (2×70 ml) and dried (MgSO$_4$). Removal of methylene chloride under vacuum afforded a yellow paste (2.0 g) which was triturated with ether and filtered to afford a light yellow solid (1.36 g, 29%, m.p. 205° C. dec.). $^1$H-NMR (CDCl$_3$, 300 MHz, $\delta$): 2H, 5, 3.0 ppm (J=6.0 Hz); 2H, t, 3.35 ppm (J=6.0 Hz); 2H, s, 3.72 ppm; 2H, bs, 4.69 ppm; 1H, t, 7.4 (J=8.0 Hz); 1H, t, 7.6 (J=8.0 Hz); 1H, d, 7.69 (J=8.0 Hz); 1H, d, 7.88 (J=8.0 Hz). HRMS: Calculated—216.0719; Found—216.0688. TLC: (TLC plate pretreated with 2% triethylamine in hexane; eluant: 5% methanol in methylenechloride) R$_f$=0.23.

EXAMPLE 7

9-Amino-4-oxa-1,2,3,4-tetrahydroacridine

To a stirred solution of delta-valerolactone 1.0 g, 10.0 mmole) in methylene chloride (10 ml) at −20° C., a 1M solution of titanium(IV) chloride in methylene chloride (20 ml) was added. The reaction mixture became dark yellow in color and to it a mixture of triethylamine (2.0 g, 20 mmole) and anthranilonitrile (1.2 g, 10.0 mmlole) in methylene chloride (30 ml) were added. The reaction mixture immediately became dark in color and was allowed to warm to room temperature (about 25° C.) and stirred further for 15 hours. At the end of this period, the reaction mixture was treated with 25% aqueous NaOH (40 ml) and methylene chloride (100 ml) and was filtered through a 2 inch diatomaceous earth pad (Celite (trademark)) which was washed with methylene chloride (50 ml) and water (100 ml). The organic layer was separated, washed once with water (30 ml) and dried (anhydrous MgSO$_4$). The methylene chloride was removed under vacuum to afford an oil which was triturated with ether to give the title compound as a white solid (565 mg, 28%). $^1$H-NMR (CDCl$_3$, 300 MHz, $\delta$): 2H, m, 2.02-2.18 ppm; 2H, t, 2.63 ppm (J=6.0 Hz); 2H, t, 4.36 ppm (J=6.0 Hz); 2H, s, 4.64 ppm; 1H, t, 7.25 (J=8.0 Hz); 1H, t, 7.5 (J=8.0 Hz); 1H, d, 7.72 (J=8.0 Hz). HRMS: Calculated—200.2396; Found—200.0945. Analysis: Calculated for C$_{12}$H$_{12}$N$_2$O: 71.98% C; 6.04% H; 13.99% N. Found: 70.91% C; 6.01% H; 14.19% N. TLC: (90:10:1-methylene chloride:methanol:28% aqueous ammonia) R$_f$=0.45.

EXAMPLE 8

9-Amino-8-fluoro-4-oxa-1,2,3,4-tetrahydroacridine

Following the procedure of Example 7, but substituting 2-amino-6-fluorobenzonitrile for anthranilonitrile afforded the title compound (8%, m.p. 195°-196° C.). $^1$H-NMR (CDCl$_3$, 300 MHz, $\delta$): 2H, m, 2.06-2.2 ppm; 2H, t, 2.6 ppm (J=6.0 Hz); 2H, t, 4.37 ppm (J=6.0 Hz); 2H, bs, 5.4 ppm; 1H, dd, 6.88 (J=14.0, 7.5 Hz); 1H, m, 7.3-7.44; 1H, d, 7.56 (J=8.6 Hz). HRMS: Calculated—218.0801; Found—218.0284 TLC: (90:10:1-methylene chloride:methanol:28% aqueous ammonia) R$_f$=0.7.

EXAMPLE 9

9-Amino-7-chloro-4-oxa-1,2,3,4-tetrahydroacridine

Following the procedure of Example 7, but substituting 2-amino-5-chlorobenzonitrile for anthranilonitrile afforded the title compound (2%, m.p. 278°-279° C.). $^1$H-NMR(CDCl$_3$, 300 MHz, $\delta$): 2H, m, 2.06-2.22 ppm; 2H, 5, 2.66 ppm (J=6.0 Hz); 2H, t, 4.37 ppm (J=6.0 Hz); 2H, bs, 4.61 ppm; 1H, dd, 7.45 (J=9.0, 1.0 Hz); 1H, bs, 7.58 ppm (J=1 Hz); 1H, d, 7.66 (J=9.0 Hz). HRMS:

Calculated—234.056; Found—234.0566. TLC:(90:10:1-methylene chloride:methanol:28% aqueous ammonia) $R_f$=0.6.

EXAMPLE 10

9-Amino-4-oxa-1,2,3,4,5,6,7,8-octahydroacridine

Following the method of Example 7, but substituting 2-amino-1-cyano-1-cyclohexene for anthranilonitrile, afforded the title compound (8%, m.p. 145°). $^1$H-NMR (CDCl$_3$, 300 MHz, δ): 4H, m, 1.65-1.9 ppm; 2H, q, 2.07 ppm (J=6.0 Hz); 2H, t, 2.4 ppm (J=6.0 Hz); 2H, t, 2.5 ppm (J=6.0 Hz); 2H, t, 2.76 ppm (J=6.0 Hz); 4H, bt, 4.26 ppm. HRMS: Calculated—204.2712; Found—204.1227. TLC:(90:10:1-methylene chloride:methanol:28% aqueous ammonia) $R_f$=0.46.

EXAMPLE 11

9-Amino-2,3,7,8-tetrahydro-1H-cyclopenta[e]6H-pyrano[2'3'-b] pyridine

Following the method of Example 7, but substituting 2-amino-1-cyano-1-cyclopentene for anthranilonitrile, afforded the title compound (22%, m.p. 164° C.). $^1$H-NMR (CDCl$_3$, 300 MHz, δ): 4H, m, 2.0-2.2 ppm; 2H, t, 2.48 ppm (J=6.0 Hz); 2H, t, 2.68 ppm (J=6.0 Hz); 2H, t, 2.87 ppm (J=6.0 Hz); 2H, bs, 4.06 ppm (J=6.0 Hz); 2H, t, 4.24 ppm. HRMS: Calculated—190.1107; Found—190.1107. TLC: (90:10:1-methylene chloride methanol:28% aqueous ammonia) $R_f$=0.86.

EXAMPLE 12

2,3-Dihydrothieno[3,2-b]quinolin-9-amine

To a stirred solution of tetrahydrothiophen-3-one (1.1 g, 11 mmole) in methylene chloride (10 ml) at −78° C., a 1M solution of titanium (IV) chloride in methylene chloride (11 ml) was added. A mixture of triethylamine (2.2 g, 22 mmole) and anthranilonitrile (1.2 gms, 10.0 mmole) in methylene chloride (30 ml) was then added to the reaction mixture over a period of 5 minutes. The reaction mixture was then slowly warmed to room temperature and stirred for 2 hours. Tetrahydrothiophen-3-one (1 ml) and titanium(IV) chloride (1.0 ml) was then added to the reaction mixture and the mixture was stirred at 25° C. for 16 hours. Thereafter, the reaction mixture was quenched with 12% aqueous NaOH (100 ml) and the reaction mixture was then stirred vigorously with additional methylene chloride (300 ml). The reaction mixture was then filtered through diatomaceous earth (Celite (trademark)) and the organic phase was separated. The organic solvents were removed under vacuum to afford a residue which was loaded on a flash chromatography column. Elution with 5% methanol in methylene chloride containing 1% triethylamine, afforded the title compound (1.3 gms, 64%) which was crystallized from chloroform (560 mg, 32%, m.p. 208°-210° C.). $^1$H-NMR (CDCl$_3$, 300 MHz, δ): 4H, m, 3.4-3.56 ppm; 2H, bs, 4.51 ppm; 1H, dt, 7.37 ppm (J=7.0, 1.0 Hz); 1H, dt, 7.52 ppm (J=7.0, 1.10 ppm); 1H, dd, 7.61 ppm (J=7.0, 1.0 ppm); 1H, dd, 7.61 ppm (J=7.0, 1.0 ppm), 1H, dd, 7.86 ppm (J=7.0, 1.0 ppm). HRMS: Calculated—202.0575; Found—202.0545.

Analysis: Calculated for C$_{11}$H$_{10}$N$_2$S: 65.32% C; 4.98%H; 13.85% N; 15.85% S. Found: 65.06% C; 5.00% H; 13.79% N; 15.63% S.

EXAMPLE 13

9-Amino-1,2,3,4,5,6,7,8-octahydro-1,4-methanoacridine

To a stirred solution of norcamphor (0.9 g, 8.2 mmole) in methylene chloride (8.0 ml) at −20° C., a mixture of triethylamine (1.7 g, 16.4 mmole) and 2-amino-1-cyano-1-cyclohexene (1.0 g, 8.2 mmole) in methylene chloride (24 ml) was added and the resulting mixture was stirred at 25° C. for 15 hours. The reaction mixture was then quenched with 12% aqueous NaCH (60 ml) and was stirred vigorously with methylene chloride (60 ml). The reaction mixture was then filtered through a 2″ pad of diatomaceous earth (Celite (trademark)). The organic phase was separated, washed with water (2×50 ml) and then dried (anhydrous MgSO$_4$). Methylene chloride was then removed under reduced pressure to afford an oil which was triturated with pentane to give the title compound as a off-white solid (225 mg, 13%, m.p. 131°-133° C.). $^1$H-NMR (CDCl$_3$, 300 MHz, δ): 2H, m, 1.15-2.38 ppm; 1H, d, 1.5 ppm; 7H, m, 165-2.0 ppm; 2H, bs, 2.4 ppm; 2H, bd, 2.8 ppm; 2H, bd 3.3 ppm; 2H, s, 3.95 ppm. HRMS: Calculated—214.3096; Found—214.1466. TLC: (90:10:1-methylene chloride: methanol:28% aqueous ammonia) $R_f$=0.25

EXAMPLE 14

9-Amino-6-aza-1,2,3,4-tetrahydroacridine

Titanium(IV) chloride (1.5 ml) was added to a stirred solution of 3-amino-4-cyano-pyridine (500 mg, 4.2 mmole) and cyclohexanone (0.5 ml) in 1,2-dichloroethane (15 ml). The reaction mixture was then maintained at 90° C. for 12 hours. At the end of this period, cyclohexanone (2.0 ml) and 1,2-dichloroethane (5.0 ml) were added to the reaction mixture and the heating was continued for another 12 hours. Additional cyclohexanone (2.0 ml) and titanium tetrachloride (1.2 ml) were then added and the reaction mixture was maintained at 90° C. for 6 hours. The reaction mixture was then cooled and was quenched with 5% aqueous NaOH (250 ml) and was stirred vigorously with methylene chloride (200 ml, 25 minutes). The reaction mixture was then treated as in Example 8 to afford the title compound (170 mg, 95% pure, 20%) after flash chromatography on silica gel (eluant:95:5:1; methylene chloride:methanol:ammonium hydroxide. This material was further purified by chromatography to afford the title compound (75 mg, m.p. 180°-181° C.). $^1$H-NMR (CDCl$_3$+CD$_3$OD, 300 MHz, δ): 4H, m, 1.9 ppm; 2H, bt, 2.54 ppm; 2H, s, 2.9 ppm; 2H, bt, 2.94 ppm; 1H, d, 7.52 ppm (J=6.0 HZ); 1H, d, 8.24 ppm (J=6.0 Hz); 1H, s, 9.06 ppm. HRMS: Calculated—199.1109; Found—199.1079.

EXAMPLE 15

9-Amino-5-aza-1,2,3,4-tetrahydroacridine

Following the method of Example 14, but substituting 2-amino-3-cyano-pyridine for 3-amino-4-cyano-pyridine, afforded the title compound (38%, m.p. 225°-228° C. dec). $^1$H-NMR (CDCl$_3$+CD$_3$OD, 300 MHz, δ): 4H, bs, 1.86 ppm; 2H, bt, 2.5 ppm; 2H, bt, 2.97 ppm; 2H, vbs, 3.0-3.3 ppm; 1H, dd, 7.2 ppm (J=8.0, 4.0 Hz); 1H, dd, 8.18 ppm (J=8.0, 1-2 Hz); 1H, dd, 8.77 ppm (J=4.0, 1-2 Hz). HRMS: Calculated—199.1109; Found—199.1102.

EXAMPLE 16

9-Amino-4,5-oxaza-1,2,3,4-tetrahydroacridine

To a stirred solution of 2-amino-3-cyano-pyridine (360 mg, 3.0 mmole) and delta-valerolactone (360 mg, 3.6 mmole) in 1,2-dichloroethane (7.0 ml), titanium(IV) chloride (0.9 ml) was added and then the reaction mixture was maintained at 90° C. for 18 hours. The reaction mixture was then quenched with 15% aqueous NaOH (200 ml) and was stirred vigorously with methylene chloride (200 ml, 25 minutes). The reaction mixture was then worked up as in example 15 to afford the title compound (8%, m.p. 269°-270° C. dec.). $^1$H-NMR (CDCl$_3$+CD$_3$OD, 300 MHz, δ): 2H, q, 2.04 pp, (J=6.5 Hz); 2H, t, 2.57 ppm (J=6.5 ppm); 2H, bs, 3.76 ppm; 2H, t, 4.28 ppm (J=6.5 Hz); 1H, dd, 7.11 ppm (J=8.0, 4.0 Hz); 1H, dd, 8.16 ppm (J=8.0, 1-2 Hz); 1H, dd, 8.64 ppm (J=4.0, 1-2 Hz). HRMS: Calculated—201.0902; Found—201.0864.

EXAMPLE 17

9-Amino-4,6-oxaza-1,2,3,4-tetrahydroacridine

Following the method of Example 16, but substituting 3-amino-4-cyano-pyridine for 2-amino-3-cyano-pyridine, afforded the title compound (16%, m.p. 237°-238° C.) $^1$H-NMR (CDCl$_3$+CD$_3$OD, 300 MHz, δ): 2H, q, 2.06 ppm (J=6.5 Hz); 2H, t, 2.59 ppm (J=6.5 ppm); 2H, s, 3.56 ppm; 2H, t, 4.3 ppm (J=6.5 Hz); 1H, d, 7.56 ppm (J=6.0 Hz); 1H, d, 8.18 ppm (J=6.0 Hz); 1H, s, 8.84 ppm. HRMS: Calculated—201.0902; Found—201.0892.

EXAMPLE 18

9-Amino-5-aza-1,2,3,4-tetrahydro-1,4-methanoacridine

Following the method of Example 16, but substituting norcamphor for delta-valerolactone afforded the title compound (29%, m.p. 243°-244° C.). $^1$H-NMR (CDCl$_3$+CD$_3$OD, 300 MHz, δ): 2H, m, 1.2-1.4 ppm; 1H, bd, 1.6 ppm (J=6.0 Hz); 1H, bd, 1.81 ppm (J=6.0 Hz); 2H, m, 1.88-2.04 ppm; 2H, bs, 3.26 ppm; 1H, bs, 3.43 ppm; 1H, bs, 3.48 ppm; 1H, dd, 7.23 ppm (J=8.03, 3.0 Hz); 1H, d, 8.17 ppm (J=8.0 Hz); 1H, d, 8.76 ppm (J=3.0 Hz). HRMS: Calculated—211.1109. Found—211.1120.

EXAMPLE 19

9-Amino-6-aza-1,2,3,4-tetrahydro-1,4-methanoacridine

Following the method of Example 16, but substituting norcamphor for delta-valerolactone and 3-amino-4-cyano-pyridine for 2-amino-3-cyano-pyridine, afforded the title compound (16%, m.p. 236°-237° C.). $^1$H-NMR (CDCl$_3$+CD$_3$OD, 300 MHz, δ): 2H, bq, 1.3 ppm; 1H, bd, 1.62 ppm; 1H, bd, 1.83 ppm; 2H, m, 1.9-2.1 ppm; 2H, s, 3.4 ppm; 1H, bs, 3.42 ppm; 1H, bs, 3.5 ppm; 1H, d, 7.6 ppm (J=6.0 Hz); 1H, d, 8.31 ppm (J=6.0 Hz); 1H, s, 9.07 ppm. HRMS: Calculated—211.1109; Found—211.1103.

EXAMPLE 20

9-Cyclohexylmethylamino-8-fluoro-4-oxa-1,2,3,4-tetrahydroacridine

A mixture of sodium hydride (60% oil, 110 mg, 2.75 mmole), the title compound of Example 6 (600 mg, 2.75 mmole, cyclohexylmethyl bromide (487 mg, 2.75 mmole) and dimethylformamide (3.0 ml) were heated with stirring at 25° C. for 12 hours and then at 65° C. for 12 hours. At the end of this period, the reaction mixture was quenched by pouring it into water (45 ml) and the resulting mixture was then extracted with ethyl acetate (3×35 ml). The combined organic layer was washed with water (2×40 ml) and dried (anhydrous MgSO$_4$). The ethyl acetate was removed under vacuum to afford a residue which was loaded on a flash chromatography column packed with silica gel. Elution with ethyl acetate afforded an oil which solidified on standing. Trituration of this solid with pentane afforded the title compound (110 mg, 13%) as a tan crystalline solid (m.p. 100° C.). $^1$H-NMR (CDCl$_3$, 300 MHz δ): 2H, m, 0.9-1.04 ppm; 3H, m, 1.04-1.32 ppm; 6H, m, 1.6-1.86 ppm; 2H, m, 1.88-2.04 ppm; 2H, t, 2.79 ppm (J=6.0 Hz); 2H, bs, 3.17 ppm; 2H, t, 4.38 ppm (J=6.0 Hz); 1H, bd, 5.79 ppm (J=20 Hz); 1H, dd, 6.84 ppm (J=140, 7.5 Hz); 1H, dd, 7.32 ppm; 1H, d, 7.48 ppm (J=8.2 Hz). HRMS: Calculated—314.1759; Found—314.1787. TLC: (ethylacetate) R$_f$=0.35.

EXAMPLE 21

9-Cyclohexylethylamino-8-fluoro-4-oxa-1,2,3,4-tetrahydroacridine

Following the method of Example 20, but substituting cyclohexylethyl bromide for cyclohexylmethyl bromide, afforded the title compound (34%). $^1$H-NMR (CDCl$_3$, 300 MHz, δ): 2H, m, 0.8-1.02 ppm; 4H, m, 1.02-1.4 ppm; 2H, m, 1.44-1.56 ppm; 5H, bd, 1.56-1.8 ppm; 2H, q, 1.92-2.04 ppm (J=6.0 Hz); 2H, t, 2.8 ppm (J=6 Hz); 2H, bt, 3.33 ppm; 2H, t, 4.36 ppm (J=6 Hz); 1H, bd, 5.6 ppm (J=20 Hz); 1H, dd, 6.38 ppm (J=14.0, 7.5 Hz); 1H, dd, 7.24-7.38 ppm; 1H, d, 7.48 ppm (J=8.2 Hz). HRMS: Calculated—328.1951; Found—328.1909. Analysis: Calculated for C$_{20}$H$_{25}$N$_2$OF:73.14% C; 7.67% H; 8.53% N. Found: 73.23% C; 7.93% H; 8.52% N. TLC: (ethyl acetate) R$_f$=0.45.

EXAMPLE 22

9-Benzylamino-8-fluoro-4-oxa-1,2,3,4-tetrahydroacridine

Following the method of Example 20, but substituting benzyl bromide for cyclohexylmethyl bromide, afforded the title compound (38%, m.p. 134°-135° C.). $^1$H-NMR (CDCl$_3$, 300 MHz, δ): 2H, q, 1.98 ppm (J=6 Hz); 2H, t, 2.87 ppm (J=6.0 Hz); 2H, t, 4.37 ppm (J=6 Hz); 2H, bs, 4.48 ppm; 1 H, bd, 5.87 ppm (J=20 Hz); 1H, dd, 6.84 ppm (J=14, 7.5 Hz); 6H, m, 7.22-7.4 ppm; 1H, d, 7.52 ppm (J=8.2 Hz). HRMS: Calculated—308.1325; Found—308.1316. Analysis: Calculated for C$_{19}$H$_{17}$N$_2$OF:74.01% C; 5.56% H; 9.08% N. Found: 73.68% C; 5.61% H; 9.01% N. TLC: (ethyl acetate) R$_f$=0.37.

EXAMPLE 23

9-Phenethylamino-8-fluoro-4-oxa-1,2,3,4-tetrahydroacridine

Following the method of Example 20 but substituting (2-bromoethyl)benzene for cyclohexylmethyl bromide afforded the title compound (20%, m.p. 125°-126° C.). $^1$H-NMR (CDCl$_3$, 300 MHz, δ): 2H, q, 1.92 ppm (J=6 Hz); 2H, t, 2.69 ppm (J=6.0 Hz); 2H, m, 2.9-3.0 ppm; 2H, bt, 3.38 ppm; 2H, m, 4.3-4.42 ppm; 1H, bd, 5.96 ppm (J=20 Hz); 1H, dd, 6.78 ppm (J=14, 7.5 Hz); 1H, d, 7.14 ppm (J=8.6 Hz); 6H, m, 7.22-7.4 ppm. HRMS: Calculated—322.3809; Found—322.1486. TLC: (ethyl acetate) R$_f$=0.53.

EXAMPLE 24

9-Phenpropylamino-8-fluoro-4-oxa-1,2,3,4-tetrahydroacridine

Following the method of Example 20, but substituting 1-bromo-3-phenylpropane for cyclohexylmethyl bromide, afforded the title compound (53% oil). $^1$H-NMR (CDCl$_3$, 300 MHz, $\delta$): 4H, m, 1.82–2.02 ppm; 4H, m, 2.62–2.78 ppm; 2H, bs, 2.34 ppm; 2H, t, 4.35 ppm (J=6.0 Hz); 1H, bd, 5.7 ppm (J=20 Hz); 1H, 6.86 ppm (J=14, 7.5 Hz); 6H, m, 7.04–7.4 ppm; 1H, d, 7.51 ppm (J=8.2 Hz). HRMS: Calculated—336.1638; Found—336.1649. TLC: (ethyl acetate) R$_f$=0.38.

EXAMPLE 25

9-(3,3-Diphenylpropylamino)-8-fluoro-4-oxa-1,2,3,4-tetrahydroacridine

Following the method of Example 20, but substituting 1bromo-3,3-diphenylpropane for cyclohexylmethyl bromide, afforded the title compound (32%, m.p. 134°–135° C.). $^1$H-NMR (CDCl$_3$, 300 MHz, $\delta$): 2H, q, 1.9 ppm (J=6 Hz); 2H, q, 2.36 ppm (J=6.0 Hz); 2H, t, 2.51 ppm (J=6 Hz); 2H, bs, 3.32 ppm; 1H, t, 4.0 (J=6 Hz); 2H, t, 4.31 ppm (J=6 Hz); 1H, bs, 5.72 ppm (J=20 Hz); 1H, dd, 6.9 ppm (J=14.0, 7.5 Hz); 10H, m, 7.1–7.3 ppm; 1H, dd, 7.3–7.4 ppm; 1H, d,7.52 ppm (J=8.2 Hz). HRMS: Calculated—412.1951; Found—412.2004.

Analysis: Calculated for C$_{27}$H$_{25}$N$_2$OF: 78.62% c; 6.11% H; 6.79% N. Found: 78.08% C; 5.95% H; 6.70% N. TLC: (ethyl acetate) R$_f$=0.48.

EXAMPLE 26

9-Amino-4-thia-1,2,3,4-tetrahydroacridine

Following the method of Example 7, but substituting delta-thiovalerolactone for delta-valerolactone afforded the title compound (4%, m.p. 190° C.). $^1$H-NMR (CDCl$_3$, 300 MHz, $\delta$): 2H, m, 2.22–2.3 ppm; 2H, t, 2.73 ppm (J=6.5 Hz); 2H, m, 3.1–3.2 ppm; 2H, bs, 4.66 ppm; 1H, t, 7.32 ppm (J=8 Hz); 1H, t, 7.54 ppm (J=8 Hz); 1H, d, 7.62 ppm (J=8 Hz); 1H, d, 7.8 ppm (J=8 Hz). HRMS: Calculated—216.0723; Found—216.0735. TLC: (90:10:1-methylene chloride: methanol: 28% aqueous ammonia) R$_f$-0.61.

EXAMPLE 27

9-Amino-3-methyl-4-oxa-1,2,3,4-tetrahydroacridine

Following the method of Example 7, but substituting 6-methyl-tetrahydropyran-2-one for delta-valerolactone, afforded the title compound (23%, m.p. 202°–203° C.). $^1$H-NMR (CDCl$_3$, 300 MHz,$\delta$): 3H, d, 1.45 ppm (J=6.5 Hz); 1H, m, 1.7–1.84 ppm; 1H, m, 2.04–2.18 ppm; 2H, m, 2.58–2.64 ppm; 1H,4.22–4.36 ppm; 2H, bs, 4.69 ppm; 1H, t, 7.22 ppm (J=7.5 Hz); 1H, t, 7.47 ppm (J=7.5 Hz); 1H, d, 7.58 ppm (J=7.5 Hz); 1H, d, 7.71 ppm (J=7.5 Hz). HRMS: Calculated—214.269; Found—214.1138.

EXAMPLE 28

9-Amino-3-methyl-8-fluoro-4-oxa-1,2,3,4tetrahydroacridine

Following the method of Example 7, but substituting 6-methyl-tetrahydropyran-2-one for delta-valerolactone and 2-amino-6-fluorobenzonitrile for anthranilonitrile afforded the title compound (13%, m.p. 217–218° C.). $^1$H-NMR (CDCl$_3$, 300 MHz,$\delta$): 3H, d, 1.45 ppm (J=6.5 Hz); 1H, m, 2.65–2.84 ppm; 1H, m, 2.06–2.19 ppm; 2H, m, 2.5–2.6 ppm: 1H, m, 4.21–4.38 ppm; 2H, bs, 5.25 ppm; 1H, dd, 6.8 ppm (J=7.5, 14 Hz); 1H, dd, 7.32 ppm (J=8 Hz, 14.0 Hz); 1H, d, 7.5 ppm (J=8 Hz). HRMS: Calculated—232.1026; Found—232.1012 TLC: (90:10:1-methylene chloride: methanol: 28% aqueous ammonia) R$_f$—0.76.

EXAMPLE 29

9-Amino-8-fluoro-2-thia-1,2,3,4-tetrahydroacridine

Following the method of Example 7, but substituting tetrahydrothiopyran-4-one for delta-valerolactone and 2-amino-6-fluorobenzonitrile for anthranilonitrile, afforded the title compound (19%, m.p. 175°–176° C.). $^1$H-NMR (CDCl$_3$, 300 MHz, $\delta$): 2H, t, 2.96 ppm (J=6.2 Hz); 2H, t, 3.3 ppm (J=6.2 Hz); 2H, s, 3.6 ppm; 2H, bs, 5.34 ppm; 1H, dd, 6.94 ppm (J=6.2, 14 Hz); 1H, dd, 7.42 ppm (J=8.6, 14 Hz); 1H, d, 7.61 ppm (J=8.6 Hz). HRMS: Calculated—234.067; Found—234.0605; TLC: (ethyl acetate) R$_f$0.23.

EXAMPLE 30

9-Amino-1,2,3,4-tetrahydro-1,4-ethanoacridine

Following the method of Example 1, but substituting bicyclo [2.2.2]octan-2-one for norcamphor afforded the title compound (20%, m.p. 197°–199° C.). $^1$H-NMR (CDCl$_3$, 300 MHz,$\delta$): 2H, m, 1.4–1.58 ppm; 2H, m, 1.58–1.74 ppm; 4H, m, 1.8–2.0 ppm; 2H, bs, 3.2 ppm; 2H, bs, 4.65 ppm; 1H, t, 7.4 ppm (J=8.5 Hz); 1H, t, 7.58 ppm (J=8.5 Hz); 1H, d, 7.71 ppm (J=8.5 Hz); 1H, 7.97 ppm (J=8.5 Hz). TLC: (90:10:1-methylene chloride:-methanol:28% aqueous ammonia) R$_f$0.35.

EXAMPLE 31

2,3-Dihydrofuro[2,3-b]quinolin-4-amine

Following the method of Example 7, but substituting gamma-butyrolactone for delta-valerolactone afforded the title compound (m.p. 300° C. dec). $^1$H-NMR (CDCl$_3$, 300 MHz,$\delta$): 2H, t, 3.17 ppm (J=8 Hz); 2H, bs, 4.6 ppm; 2H, t, 4.69 ppm (J=8 Hz); 1H, t, 7.28 ppm (J=8 Hz); 1H, t, 7.53 ppm (J=8 Hz); 1H, d, 7.62 ppm (J=8 Hz); 1H, d, 7.77 ppm (J=8 Hz). LRMS: Found—186.

EXAMPLE 32

6H-[1]Benzopyrano[4,3-b]quinolin-7-amine

Following the method of Example 7, but substituting 4-chromanone for delta-valerolactone afforded the title compound (3%, m.p. 275° C. dec). $^1$H-NMR (DMSO, 300 MHz,$\delta$): 2H, s, 5.3 ppm; 1H, d, 6.97 ppm (J=8.2 Hz); 1H, t, 7.08 ppm (J=7.0 Hz); 2H, m, 7.15–7.4 ppm; 1H, t, 7.57 ppm (J=7.0 Hz); 1H, d, 7.78 ppm (J=7.0 Hz); 1H, d, 8.16 ppm (J=8.0 Hz); 1H, dd, 8.24 ppm (J=7.0, 2.0 Hz). HRMS: Calculated—248.287; Found—248.0908; TLC: (90:10:1-methylene chloride:methanol:28% aqueous ammonia) R$_f$0.65.

EXAMPLE 33

6H-[1]Benzothiopyrano[4,3-b]quinolin-7-amine

Following the method of Example 7, but substituting thiochroman-4-one for delta-valerolactone afforded the title compound (13%, m.p. 211°–212° C.). $^1$H-NMR (CDCl$_3$, 300 MHz,$\delta$): 2H, s, 3.94 ppm; 2H, bs 4.7 ppm; 4H, m, 7.23–7.44 ppm; 1H, t, 7.61 ppm (J=7 Hz); 1H, d, 7.7 ppm (J=7 Hz); 1H, d, 8.02 ppm (J=7.0 Hz); 1H, 8.5 ppm (J=7.0,2.0 Hz). HRMS: Calculated—264.0721;

Found—264.0715; TLC: (90:10:1-methylene chloride:-methanol:28% aqueous ammonia) R$_f$-0.77.

EXAMPLE 34

9-Methylamino-8-fluoro-4-oxa-1,2,3,4-tetrahydroacridine

Following the method Example 20, but substituting iodomethane for cyclohexylmethyl bromide afforded the title compound (for HCl salt: m.p. 240° C.). $^1$H-NMR (DMSO, 300 MHz,$\delta$): 2H, m, 2.0 ppm; 2H, t, 2.95 ppm (J=6.5 Hz); 3H, bd, 3.3 ppm; 2H, t, 4.53 ppm (J=6.5 Hz); 1H, dd, 7.34 ppm (J=8, 14 Hz); 1H, dd, 7.44 ppm (J=8.0 Hz); 1H, m, 7.7–7.8 ppm; 1H, bm, 7.94–8.06 ppm.

EXAMPLE 35

2,3-Dihydro-8-fluorothieno[3,2-b]quinolin-9-amine (Compound A) and 1,3-Dihydro-8-fluoro-thieno[3,4-b]quinolin-9-amine (Compound B)

Following the method of Example 12 but substituting 2-amino-6-fluorobenzonitrile for anthranilonitrile afforded a 1:1 mixture of the two title compounds. Compound A (m.p. 137° C.): $^1$H-NMR (CDCl$_3$, 300 MHz,$\delta$): 4H, m, 3.48 ppm; 2H, bs, 5.09 ppm; 1H, dd, 6.98 ppm (J=7.3, 14.5 Hz); 1H, dd, 7.38 ppm (J=7.3, 10.5 Hz); 1H, d, 7.64 ppm (J=10.5 Hz); TLC: (ethyl acetate) R$_f$-0.38. Compound B (m.p. 198° C. dec.) $^1$H-NMR (CDCl$_3$, 300 MHz,$\delta$): 2H, s, 4.09 ppm; 2H, s, 4.38 ppm; 2H, bs, 5.3 ppm; 1H, dd, 7.0 ppm (J=7.3, 14.5 Hz); 1H, dd, 7.47 ppm (J=7.3, 10.5 Hz); 1H, d, 7.68 ppm (J=10.5 Hz); TLC: (ethyl acetate) R$_f$-0.49.

EXAMPLE 36

9-Amino-1,2-dihyroacridine-4(3H)-one

Following the method of Example 1, but substituting 1,2-cyclohexanedione for norcamphor, afforded the title compound (11%, m.p. 240° C. dec.). $^1$H-NMR (CDCl$_3$, 300 MHz,$\delta$): 2H, quin, 2.31 ppm; 4H, mt, 2.8–2.95 ppm; 2H, bs, 4.95 ppm; 1H, t, 7.29 ppm (J=8.5 Hz); 1H, t, 7.64 ppm (J=8.5 Hz); 1H, d, 7.74 ppm (J=8.5 Hz); 1H, d, 8.2 ppm (J=8.51 Hz); HRMS: Calculated—212.0950; Found—212.0941; TLC: (90:10:1-methylene chloride:methanol:28% aqueous ammonia) R$_f$-0.41.

EXAMPLE 37

8-fluoro-9-amino-1,2,3,4-tetrahydroacridine

To a stirred solution of cyclohexanone (1.0 g, 10.0 mmole) in methylene chloride (10 ml) at −20° C., a 1M solution of titanium (IV) chloride in methylene chloride (20 ml) was added. The reaction mixture became yellow in color and to it a mixture of triethylamine (2.0 g, 20 mmole) and 2-amino-6-fluorobenzonitrile (1.36 g, 10.0 mmole) in methylene chloride (30 ml) were added. The reaction mixture immediately became dark in color and was allowed to warm to room temperature (about 25° C.) and stirred further for 15 hours. At the end of this period, the reaction mixture was treated with 12% aqueous NaOH (100 ml), and methylene chloride (100 ml). The reaction mixture was then filtered through a 2 inch diatomaceous earth pad (Celite (trademark)) which was washed with methylene chloride (50 ml) and water (100 ml). The organic layer was separated, washed with water (1×30 ml) and dried (anhydrous MgSO$_4$). The methylene chloride was removed under vacuum to afford an oil which was triturated with ether to give the title compound as a white solid (218 mg, 10%, m.p. 175° C.). $^1$H-NMR (CDCl$_3$, 300 MHz,$\delta$): 4H, m, 2.0 ppm; 2H, t, 2.59 ppm (J=7.0 Hz); 2H, t, 3.06 ppm (J=7.0 Hz); 2H, bs, 5.37 ppm; 1H, dd, 7.0 ppm (J=7.5, 14 Hz); 1H, dd, 7.46 ppm (J=8, 16 Hz); 1H d, 7.72 ppm (J=8.5 Hz). HRMS: Calculated—216.1053; Found—216.1039.

EXAMPLE 38

9-Amino-8-methyl-1,2,3,4-tetrahydroacridine

Following the method of Example 37, but substituting 2-amino-6-methylbenzonitrile for 2-amino-6-fluorobenzonitrile, afforded the title compound (11%, m.p. 143°–145° C.). $^1$H-NMR (CDCl$_3$, 300 MHz, $\delta$): 1H, d, 7.68 ppm (J=8 Hz); 1H, t, 7.34 ppm (J=8 Hz); 1H, d, 7.02 ppm (J=8 Hz); 2H, bs, 4.89 ppm; 2H, t, 2.95 (J=6 Hz); 3H, s, 2.92 ppm; 2H, t, 2.49 ppm (J=6 Hz); 4H, m, 1.8–2.0 ppm; HRMS: Calculated—212.1313; Found—212.1273; TLC: (90:10:1-methylene chloride:methanol:28% aqueous ammonia) R$_f$-0.23.

EXAMPLE 39

9-Amino-8-chloro-1,2,3,4-tetrahydroacridine

Following the method of Example 37, but substituting 2-amino-6-chlorobenzonitrile for 2-amino-6-fluorobenzonitrile, afforded the title compound (23%, m.p. 144°–145° C.). $^1$H-NMR (CDCl$_3$, 300 MHz,$\delta$): 1H, d, 7.75 ppm (J=8 Hz); 1H, t, 7.35 ppm (J=8 Hz); 1H, d, 7.27 ppm (J=8 Hz); 2H, bs, 5.81 ppm; 2H, t, 2.96 ppm (J=6 Hz); 2H, t, 2.49 ppm (J=6 Hz); 4H, m, 1.96–1.86 ppm; HRMS: Calculated—232.0770; Found—232.0777; TLC: (90:10:1-methylene chloride:methanol:28% aqueous ammonia) R$_f$-0.62.

EXAMPLE 40

4-Amino-5-fluoro-2,3-pentamethylenequinoline

Following the method of Example 37, but substituting cycloheptanone for cyclohexanone, afforded the title compound (22%, m.p. 203° C.). $^1$H-NMR (CDCl$_3$, 300 MHz,$\delta$): 1H, d, 7.67 ppm (J=8 Hz); 1H, dd, 7.39 ppm (J=8 Hz); 1H, dd, 6.96 ppm (J=7, 14 Hz); 2H, bs, 5.34 ppm; 2H, m, 3.09 ppm; 2H, m, 2.7 ppm; 6H, m, 1.6–2.0 ppm; HRMS: Calculated—230.1219; Found—230.1235; TLC: (ethyl acetate) R$_f$-0.31.

EXAMPLE 41

4-Amino-5-chloro-2,3-pentamethylenequinoline

Following the method of Example 37, but substituting cycloheptanone for cyclohexanone and 2-amino-6-chlorobenzonitrile for 2-Amino-6-fluorobenzonitrile, afforded the title compound (11%, m.p. 194°–195° C.). $^1$H-NMR (CDCl$_3$, 300 MHz,$\delta$): 1H, d, 7.79 ppm (J=7 Hz); 2H, m, 7.30–7.39 ppm; 2H, bs, 5.85 ppm; 2H, m, 3.08 ppm; 2H, m, 2.69 ppm; 6H, m, 1.65–2.0 ppm; HRMS: Calculated—246.0924; Found—246.0914; TLC: (ethyl acetate) R$_f$-0.34.

EXAMPLE 42

4-Amino-5-fluoro-2,3-trimethylenequinoline

Following the method of Example 37, but substituting cyclopentanone for cyclohexanone, afforded the title compound (6%, m.p. 179°–181° C.). $^1$H-NMR (CDCl$_3$, 300 MHz,$\delta$): 1H, d, 7.65 ppm (J=8 Hz); 1H, dd, 7.4 Hz (J=8 Hz); 1H, dd, 6.93 ppm (J=7.14 Hz); 1H, bs, 5.10 ppm; 2H, t, 3.07 ppm (J=8 Hz); 2H, t, 2.8 ppm (J=8 Hz); 2H, quin, 2.1–2.23 ppm (J=8 Hz);

HRMS: Calculated—202.0906; Found—202.0909; TLC: (90:10:1-methylene chloride:methanol:28% aqueous ammonia) $R_f$ 0.52.

EXAMPLE 43

9-Amino-8-chloro-4-oxo-1,2,3,4-tetrahydroacridine

Following the method of Example 7, but substituting 2-amino-6-chlorobenzonitrile for anthranilonitrile, afforded the title compound (15%, m.p. 205° C.). $^1$H-NMR (CDCl$_3$, 300 MHz,δ): 1H, d, 7.62 ppm (J=7 Hz); 1H, t, 7.31 ppm (J=7 Hz); 1H, d, 7.19 ppm (J=7 Hz); 2H, bs, 5.81 ppm; 2H, t, 4.31 ppm (J=6 Hz); 2H, t, 2.52 ppm (J=6 Hz); 2H, m, 2.11 ppm; HRMS: Calculated—234.0560; Found—234.0565; TLC: (ethyl acetate) $R_f$ 0.27.

EXAMPLE 44

9-Amino-8-methyl-4-oxa-1,2,3,4-tetrahydroacridine

Following the method of Example 7, but substituting 2-amino-6-methylbenzonitrile for anthranilonitrile, afforded the title compound (20%, m.p. 177°-179° C.). $^1$H-NMR (CDCl$_3$, 300 MHz,δ): 1H, d, 7.56 ppm (J=7 Hz); 1H, t, 7.31 ppm (J=7 Hz); 1H, d, 6.95 ppm (J=7 Hz); 2H, bs, 4.93 ppm; 2H, t, 4.29 ppm (J=6 Hz); 3H, s, 2.89 ppm; 2H, t, 2.52 ppm (J=6 Hz); 2H, m, 2.08-2.11 ppm; HRMS: Calculated—214.1106; Found—214.1097; TLC: (ethyl acetate) $R_f$ 0.27.

EXAMPLE 45

9-Amino-8-methoxy-1,2,3,4-tetrahydroacridine

Following the method of Example 37, but substituting 2-amino-6-methoxybenzonitrile for 2-amino-6-fluorobenzonitrile, afforded the title compound (14%, m.p. 187°-188° C.). $^1$H-NMR (CDCl$_3$, 300 MHz,δ): 1H, d, 7.45 ppm (J=8.0 Hz); 1H, t, 7.37 ppm (J=8 Hz); 1H, d, 6.64 ppm (J=8 Hz); 1H, bs, 5.88 ppm; 3H, s, 3.96 ppm; 2H, t, 2.95 ppm (J=7 Hz); 2H, t, 2.46 ppm (J=7 Hz); 4H, m, 1.94-1.85 ppm; HRMS: Calculated—228.1233; Found—228.1277; TLC: (90:10:1-methylene chloride:methanol:28% aqueous ammonia) $R_f$ 0.20.

EXAMPLE 46

9-Amino-8-methoxy-4-oxa-1,2,3,4-tetrahydroacridine

Following the method of Example 7, but substituting 2-amino-6-methoxybenzonitrile for anthranilonitrile afforded the title compound (11%, m.p. 205°-207° C.). $^1$H-NMR (CDCl$_3$, 300 MHz,δ): 2H, m, 7.33 ppm; 1H, dd, 6.57 ppm (J=3, 6 Hz); 2H, bs, 5.92 ppm; 2H, t, 4.29 ppm (J=2, 6 Hz); 3H, s, 3.95 ppm; 2H, t, 2.5 ppm (J=2, 6 Hz); 2H, m, 2.13-2.07 ppm; TLC: (90:10:1-methylene chloride:methanol:28% aqueous ammonia) $R_f$ 0.49.

EXAMPLE 47

The ability of the title compounds of Examples 1-16, 18, 26-29, and 35-46 to inhibit brain acetylcholinesterase was determined by the spectrophotometric method of G. L. Ellman et al. (*Biochemical Pharmacology*, 7, 88 (1961)). All of the compounds had IC$_{50}$ (molar) values between 5 μM and 0.1 μM.

I claim:

1. A compound selected from the group consisting of: 9-amino-4-oxa-1,2,3,4-tetrahydroacridine; 9-amino-2-oxa-1,2,3,4,-tetrahydroacridine; 9-amino-8-fluoro-4-oxa-1,2,3,4-tetrahydroacridine; 9-amino-4-oxa-1,2,3,4,5,6,7,8-octahydroacridine; or a pharmaceutically acceptable salt thereof.

* * * * *